US010342640B2

(12) United States Patent
Cassalia

(10) Patent No.: US 10,342,640 B2
(45) Date of Patent: Jul. 9, 2019

(54) ORTHODONTIC WIRE ALIGNMENT SYSTEM AND METHOD

(71) Applicant: Benjamin Cassalia, Ottsville, PA (US)

(72) Inventor: Benjamin Cassalia, Ottsville, PA (US)

( * ) Notice: Subject to any disclaimer, the term of this patent is extended or adjusted under 35 U.S.C. 154(b) by 376 days.

(21) Appl. No.: 14/244,985

(22) Filed: Apr. 4, 2014

(65) Prior Publication Data

US 2014/0302448 A1    Oct. 9, 2014

Related U.S. Application Data

(60) Provisional application No. 61/808,953, filed on Apr. 5, 2013.

(51) Int. Cl.
| | | |
|---|---|---|
| *A61C 7/28* | (2006.01) | |
| *A61C 7/12* | (2006.01) | |
| *A61C 7/14* | (2006.01) | |
| *A61C 7/20* | (2006.01) | |

(52) U.S. Cl.
CPC ............... *A61C 7/28* (2013.01); *A61C 7/12* (2013.01); *A61C 7/145* (2013.01); *A61C 7/146* (2013.01); *A61C 7/20* (2013.01)

(58) Field of Classification Search
CPC .... A61C 7/282; A61C 7/12–7/34; A61C 7/00; A61C 7/145
USPC ........................................................ 433/8–24
See application file for complete search history.

(56) References Cited

U.S. PATENT DOCUMENTS

| | | | |
|---|---|---|---|
| 4,217,264 A | | 8/1980 | Mabie et al. |
| 4,936,774 A | * | 6/1990 | Stoller .................... A61C 7/12 |
| | | | 433/110 |
| 5,183,403 A | * | 2/1993 | Masuhara ................ A61C 7/00 |
| | | | 433/8 |
| 5,350,203 A | * | 9/1994 | McNaughton ...... F16L 33/2075 |
| | | | 285/305 |
| 5,522,725 A | * | 6/1996 | Jordan .................... A61C 7/12 |
| | | | 433/8 |
| 5,595,484 A | | 1/1997 | Orikasa et al. |
| 6,358,043 B1 | * | 3/2002 | Mottate .................. A61C 7/141 |
| | | | 433/20 |

(Continued)

FOREIGN PATENT DOCUMENTS

WO    01/82821 A1    11/2011

OTHER PUBLICATIONS

International Search Report & Written Opinion for the International Patent Application No. PCT/US2014/032918 dated Sep. 11, 2014.

(Continued)

*Primary Examiner* — Matthew M Nelson

(74) *Attorney, Agent, or Firm* — Caesar Rivise, PC

(57) ABSTRACT

Disclosed is a system and method for treating mal-alignment of teeth using super-elastic nickel titanium, heat activated nickel titanium coated or uncoated orthodontic wires with composite resins in order to effectuate desired tooth alignment. The composite resin is formed into beads that hold the wire in place preferably on the lingual surface of the teeth. Alternate embodiments using composite brackets are disclosed. The overall purpose of this invention is to provide a close contact, low profile orthodontic system, in particular, a lingual orthodontic system that is significantly more comfortable than existing orthodontic systems, completely concealed and effective.

12 Claims, 12 Drawing Sheets

(56) References Cited

U.S. PATENT DOCUMENTS

| | | | |
|---|---|---|---|
| 6,575,747 B1* | 6/2003 | Riitano | A61C 5/44 433/102 |
| 6,779,937 B1* | 8/2004 | Lombardi | A45D 40/205 401/6 |
| 7,160,106 B2 | 1/2007 | Farzin-Nia et al. | |
| 2002/0187453 A1* | 12/2002 | Clark | A61C 7/00 433/18 |
| 2003/0190577 A1* | 10/2003 | Shin | A61C 7/16 433/9 |
| 2004/0029067 A1* | 2/2004 | Wool | A61C 7/20 433/20 |
| 2004/0154133 A1* | 8/2004 | Polzin | B25F 5/006 16/430 |
| 2004/0157184 A1* | 8/2004 | Reising | A61C 7/146 433/8 |
| 2004/0259054 A1* | 12/2004 | Mayer | A61C 17/20 433/119 |
| 2005/0003324 A1* | 1/2005 | Reising | A61C 7/146 433/50 |
| 2005/0191592 A1* | 9/2005 | Farzin-Nia | A61C 7/00 433/22 |
| 2005/0244777 A1* | 11/2005 | Schultz | A61C 7/282 433/17 |
| 2006/0084032 A1* | 4/2006 | Tipton | A61C 3/00 433/141 |
| 2006/0110703 A1* | 5/2006 | Bills | A61C 5/42 433/102 |
| 2007/0087302 A1* | 4/2007 | Reising | A61C 7/145 433/24 |
| 2010/0239992 A1 | 9/2010 | Brandt et al. | |
| 2011/0039225 A1* | 2/2011 | Hagelganz | A61C 7/14 433/17 |
| 2011/0053108 A1* | 3/2011 | Ariza | A61C 7/282 433/17 |
| 2011/0129786 A1 | 6/2011 | Chun et al. | |
| 2011/0269091 A1 | 11/2011 | Li et al. | |
| 2011/0300502 A1* | 12/2011 | Kishi | A61C 7/28 433/10 |
| 2011/0311934 A1* | 12/2011 | Kantomaa | A61C 7/143 433/10 |
| 2012/0225398 A1 | 6/2012 | Fallah | |
| 2013/0224676 A1 | 8/2013 | Alauddin et al. | |
| 2014/0227653 A1* | 8/2014 | Kalkhoran | A61C 7/20 433/8 |

OTHER PUBLICATIONS

Supplementary Partial European Search Report for the European Patent Application No. 14779062.0 dated Dec. 6, 2016.

* cited by examiner

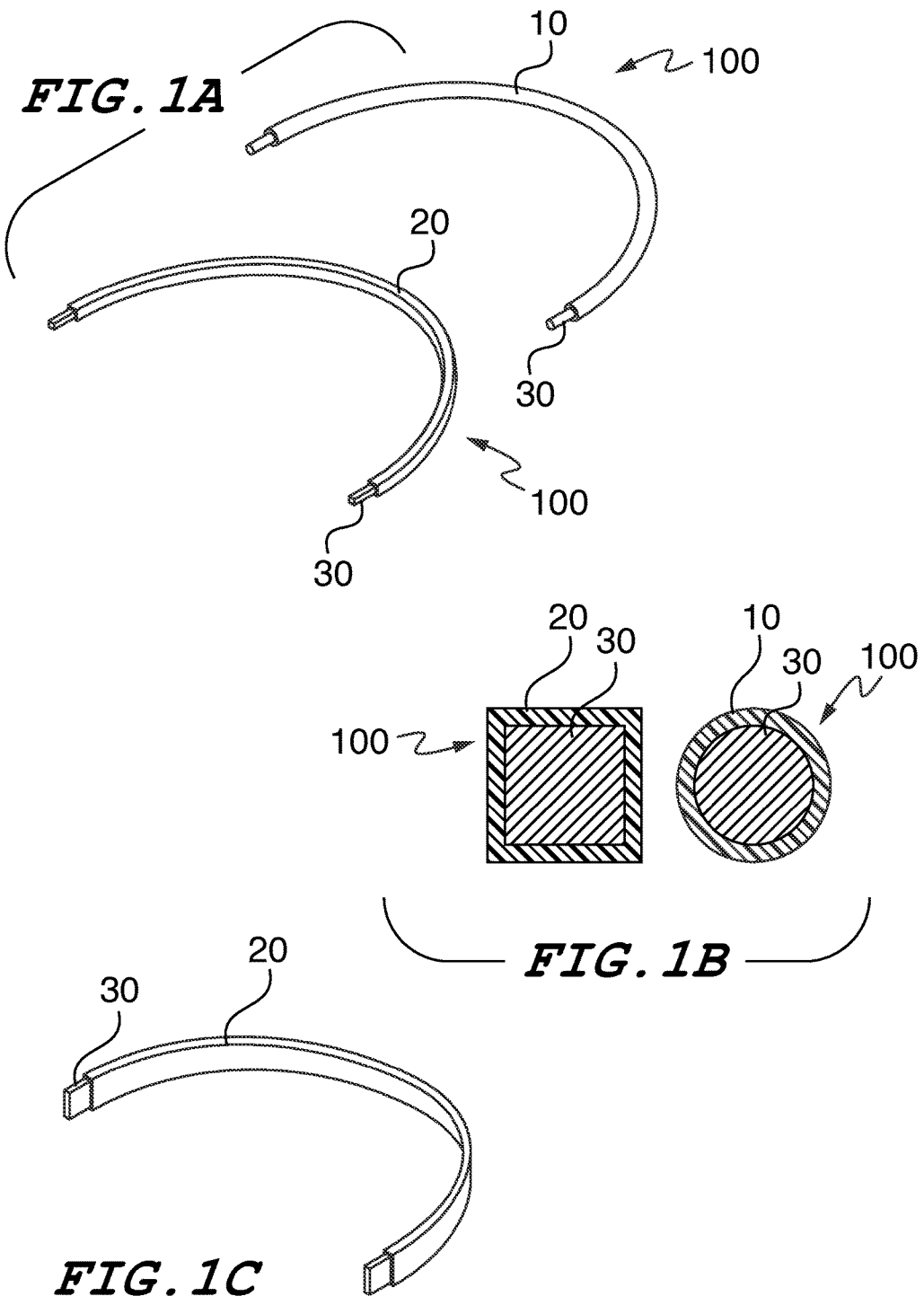

FIG.2
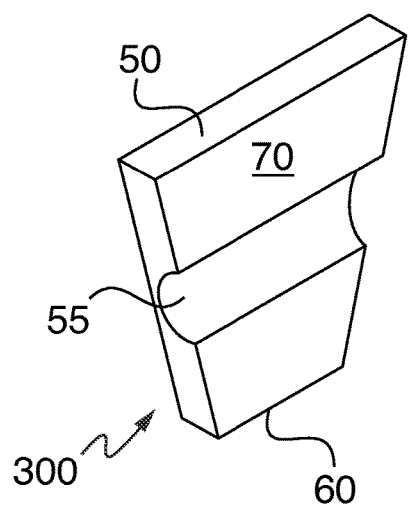
FIG.2A
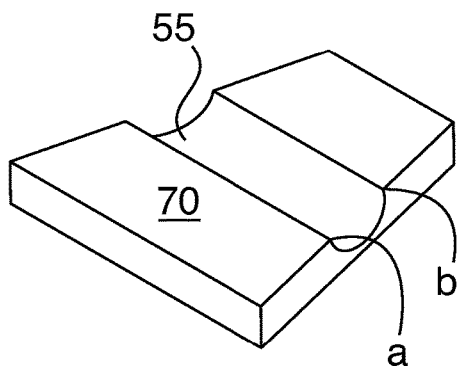
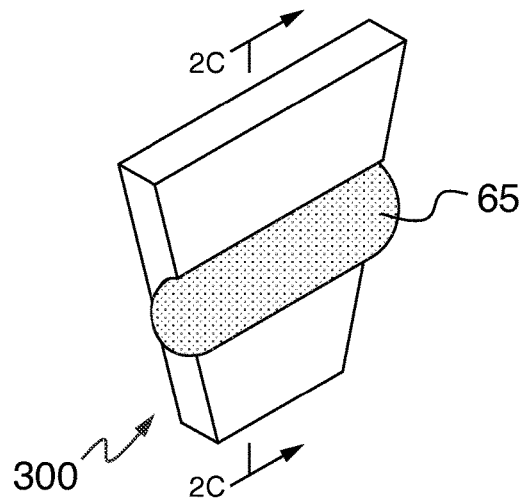
FIG.2B
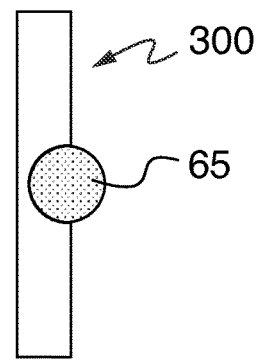
FIG.2C

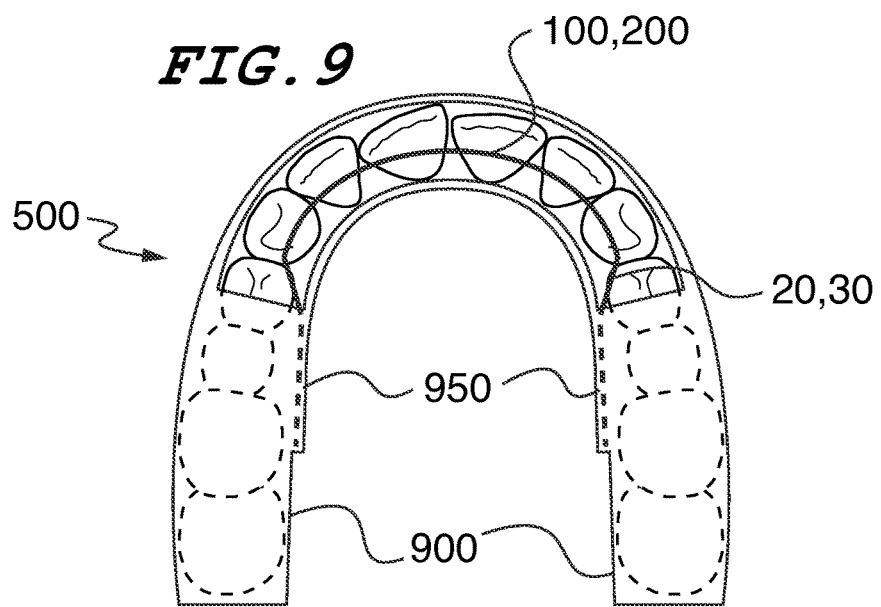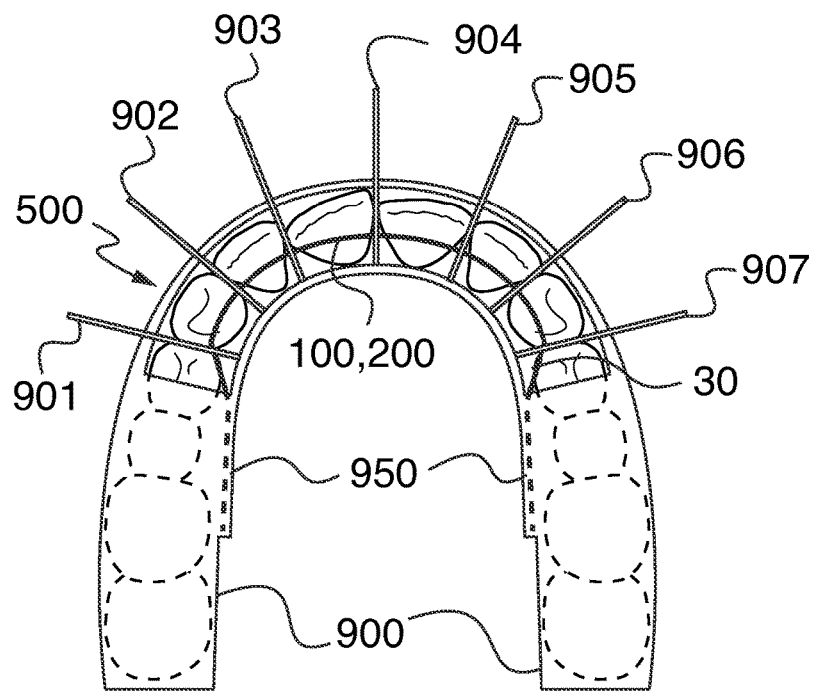

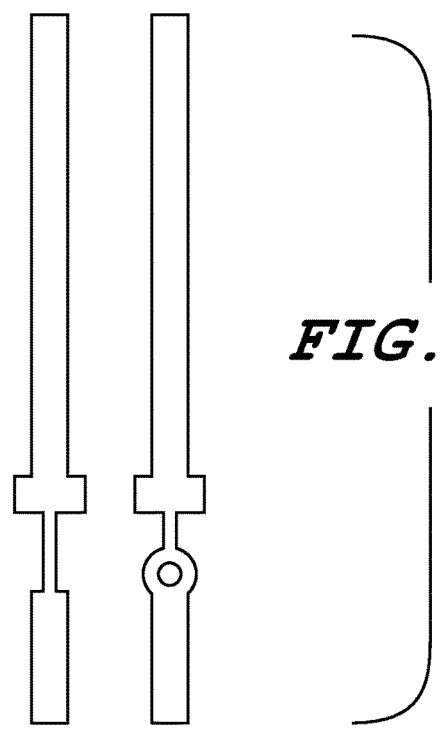
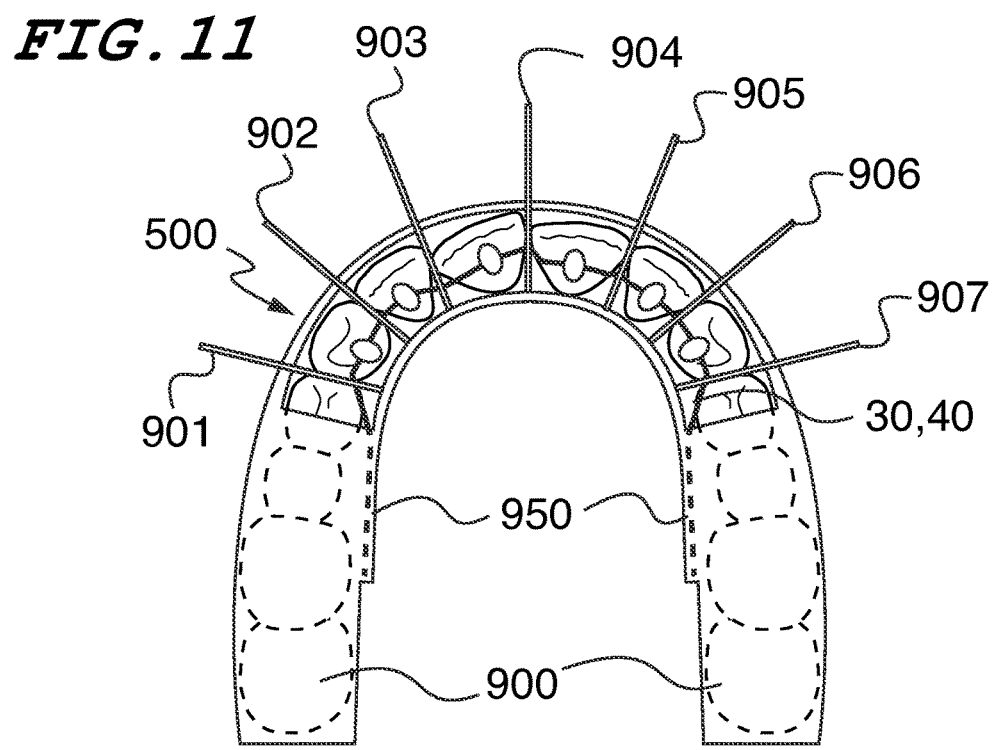

ORTHODONTIC WIRE ALIGNMENT SYSTEM AND METHOD

CROSS REFERENCE TO RELATED PATENT APPLICATIONS

The application claims the benefit of prior provisional U.S. Patent Application No. 61/808,953.

FEDERALLY SPONSORED RESEARCH OR DEVELOPMENT

The present invention was not developed with any federal funds, but was developed independently by the inventor.

FIELD OF INVENTION

The present invention relates to the field of orthodontics. More specifically, the present invention relates to systems and methods for treating mal-alignment of teeth using super-elastic nickel titanium, heat activated nickel titanium coated or uncoated orthodontic wires with composite resins in order to effectuate desired tooth alignment.

BACKGROUND OF THE INVENTION

Orthodontic treatment is a specialty of dentistry that focuses on the treatment of dental displacement and mal-alignment or misalignment of teeth. Comprehensive orthodontic treatment most commonly involves the use of metal wires that are inserted into orthodontic brackets, which can be made from stainless steel or ceramic materials. The metal wires interact with the brackets to exert continual force on the teeth to gradually urge the teeth toward their intended positions.

More recently, alternatives to conventional orthodontic treatment with traditional braces have become available. For example, systems including a series of preformed appliances/aligners have become commercially available from Align Technology, Inc., San Jose, Calif., under the trade name Invisalign® System. The Invisalign® System is described in numerous patents and patent applications including, for example in U.S. Pat. Nos. 6,450,807, and 5,975,893, as well as on the company's website, which is accessible on the World Wide Web (see, e.g., the url invis-align.com"). The Invisalign® System includes designing and/or fabricating multiple, and sometimes all, of the aligners to be worn by the patient before the aligners are administered to the patient and used to reposition the teeth (e.g., at the outset of treatment). Often, designing and planning a customized treatment for a patient makes use of computer-based 3-dimensional planning/design tools, such as Treat™ software from Align Technology, Inc. The design of the aligners relies on computer modeling of the patient's teeth in a series of planned successive tooth arrangements, and the individual aligners are designed to be worn over the teeth, such that each aligner exerts force on the tooth and elastically repositions the teeth to each of the planned tooth arrangements.

Another orthodontic option is disclosed in U.S. patent application Ser. No. 13/470,681 to Li et al., also assigned to Align Technology. Disclosed is multilayer orthodontic positioning appliance which includes a removable orthodontic tooth positioning appliance having teeth receiving cavities shaped to directly receive at least some of the patient's teeth and apply a resilient positioning force to the patient's teeth. The multilayer appliances can include a hard polymer layer disposed between two soft polymer layers. The orthodontic treatment provides improved material performance, stress relaxation properties and a longer working range.

An alternative orthodontic technology is the LingualWire-lign® and Wirelign® technique of Benjamin A. Cassalia, Chalfont, Pa., which provides a system to correct mal-alignment of teeth using wires alone (that is, without orthodontic brackets) for increased patient comfort and a look without visible "braces" or wires on the facial surface of the patient's teeth. The Wirelign® technique uses straight segments of super-elastic metal wire, usually nickel titanium wire, adhered to surfaces of teeth—usually the lingual surface (i.e. the inside surfaces of teeth, as opposed to the front, facial surfaces)—to align teeth.

In certain cases after the use of currently available orthodontic methods for correcting misaligned teeth, the alignment of teeth is improved but the proper arch form may not be obtained. For example, sometimes as teeth are pulled or pushed into alignment, undesirable tooth movements may occur, resulting in an improper arch form. One reason for certain undesirable tooth movements is that wires typically are bonded to each tooth individually at a fixed distance apart and do not permit the teeth to move closer to one another as they are pushed and/or pulled into alignment. In some cases, mal-alignment of teeth may be minor or of a type that is not easily corrected by current orthodontic procedures alone. And in some cases, continued treatment is desired to maintain or improve proper arch form.

Therefore, there is a need in the art for an orthodontic wire alignment system and method that provides improved arch form and continued alignment of teeth when used alone or after use of other orthodontic techniques, that does so in an aesthetically and cosmetically pleasing way, and is comfortable to the wearer (referred to interchangeably herein as the "patient"). The present invention provides an orthodontic system and method that is a comfortable, cosmetically pleasing means of maintaining or improving optimal arch form when used alone or after use of other orthodontic procedures.

The orthodontic system and method of the invention provide a number of advantages over previously available systems and methods. The placement of the coated wire directly to the surface of the tooth and the placement of flowable bonding material over the wire create a low profile smooth surface system compared to typical orthodontic systems that use brackets with increased profile and distance of the wire from the tooth. The smooth surface of the bonding material used in the invention compared to other brackets system with extended wings or doors minimizes irritation and discomfort to the surrounding oral tissues. The present system and method increase the effectiveness of tooth movement as a result of the close proximity of the wire to the tooth and the potential formation of an orthodontic tube along the entire surface of the tooth. These two factors provide and increase engagement of the tooth surface and therefore enable more effective tooth movement, and especially rotational movement of a tooth.

The present system also provides reduced speech related problems as compared to the prior art. The reduced profile and resulting smooth surface of the material used in the invention is comparable to already used fixed lingual retainer systems which have little to no effect of tongue manipulation and speech related problems. Furthermore, because the orthodontic system of the invention is placed preferably on the lingual surface of the teeth and has low profile characteristics, the orthodontic system of the invention is essentially completely concealed or undetected by observers. A further advantage of the system of the invention is its ease of application. The delivery system of the orthodontic system of the invention is designed for easy clinical application of the coated wire and, as such, also provides improved isolation from contaminants from the oral environment of the mouth.

One object of this invention is to improve the arch form obtained after alignment of the teeth using known orthodontic techniques. By "arch" form as used herein is meant the arch derived by the alveolar process on the jaw containing the dental anatomy of the teeth. The invention also may be used alone to correct mal-alignment of teeth if minimal to moderate tooth movement is required. The design of the arch wire system of the invention allows for the continuation of treatment for misaligned teeth using wires alone (that is, without bulky brackets or fixtures) for increased patient comfort. The wire is preferably affixed to the lingual surface of teeth such that it is not visible when the wearer smiles, thus providing a cosmetic benefit as compared to traditional orthodontic appliances or retainers. Also within the scope of the invention is use of the system of on the facial surface of teeth, albeit such use provides a lesser cosmetic advantage than use on the lingual surface of the teeth. The term "facial" herein is used to mean "non-lingual", as in the non-lingual surface of a tooth or teeth, and therefore includes "labial" and "buccal", as in the labial or buccal surface of a tooth or teeth.

SUMMARY OF THE INVENTION

A coated orthodontic wire tooth alignment system and method is used alone, after or in conjunction with known orthodontic techniques. A dissolvable coating surrounds an orthodontic wire arch form of super-elastic material such as nickel titanium. The predesigned coated-wire arch form is fixed to the lingual or facial/buccal surface of the teeth to be adjusted by flowable composite bead techniques known in orthodontics. After the composite beads cure and the coating dissolves, an aperture or tube is left around the wire within the composite beads or between the composite and the teeth, allowing the wire to move freely as it returns to its predesigned arch shape, pulling the teeth into alignment with it. Composite brackets with a lateral groove adapted to receive a coated-wire arch form aids precise positioning of the wire on the surface of the teeth. The brackets fit the contours of teeth and are placed and bonded to teeth in the desired positions before application of the arch form. Once in place, the coated wire is bonded directly to the brackets. These brackets may also have a malleable gel like substance embedded in the lateral groove in which a non-coated wire may be inserted and covered with bonding material. The same effect of a tube is formed within the composite bracket when the gel dissolves allowing for the wire to move and align the teeth. The adaption of the wire to the teeth can be direct or assisted with a delivery system that will hold the wire in position for ease of application to minimize contamination associated with the oral environment.

DETAILED DESCRIPTION OF THE INVENTION

The present invention employs wire of the same dimensions and properties as the nickel titanium wires used in typical orthodontic treatments, that is, super-elastic metal wires including those of nickel titanium or copper nickel titanium, beta titanium, and stainless steel. The wires according to the invention are most preferably super-elastic or heat activated super-elastic wires. The tensile and other physical properties of such wires when placed in the required configuration to the teeth impart a force onto the teeth that allow tooth movement to occur within the buccal cavity until the point where the desired visual effect is achieved. Preferably according to the invention, wire arch forms are pre-formed in various lengths and gauges to accommodate the needs of a variety of different patients. Though they are called "arch forms", the actual shape of the pre-formed wire arch forms may not be "arch-shaped" depending on their intended application—for example, a full-mouth lingual arch form would be mushroom shaped. The term "arch form" herein is used expansively to include any pre-shaped length of wire intended or used to correct a patient's mal-aligned teeth. The pre-shaped wire corrects improper arch form in a patient's teeth by being placed and bonded to the patient's teeth as shown in FIGS. 4 and 5. The force of the now-deformed arch wire working to regain its pre-formed arched shape pushes and pulls the patient's teeth into a shape that conforms to the arch wire, that is, the proper arch form desired. The invention permits the wire to slide longitudinally as the arch wire regains its preformed shape, thus preventing undesirable tooth movements created by affixing the wire to the each tooth a fixed distance apart.

In one embodiment of the invention, the wire is coated with a dissolvable coating, preferably a gelatin-like substance such as the gelatin coating used in medicinal liquid gel tablets or a coating having a lubricating effect such as $TiO_2$ (titanium dioxide). In a preferred embodiment, a coating particularly useful in the invention comprises titanium dioxide, starch, ethanol and lacquer. Other dissolvable media that do not hinder the elastic properties of the wire and are safe for the patient may be used.

Coatings operable within the scope of the invention include coating currently available in the dental industry, such as titanium dioxide, polyamide, cellulose derivative, or homopolymer/copolymer of poly(ethylene oxide). Other coating operable within the scope of the invention include substances commonly used in the food and the pharmaceutical industry with materials that render the substance to be delivered either more easily or pleasantly administered or more palatable to the consumer. Such coatings include, but are not limited to: alginates; biopolymers (such as xanthan gum and scleroglucan); carrageenans; galactomannans (such as locust bean gum and guar gum); pectins; native starches (such as products sold under the trademarks AmyloGel®, CreamGel™, DryGel™, Gel™); thinned starches (such as Cargill Set™ and Cargill DrySet®); stabilized starches (such as Cargill Tex®, CreamTex®, PolarTex® and StabiTex®); Pregelatinized starches including roll-dried starches (such as Cargill Tex-Instant™, Gel-Instant™, StabiTex-Instant®, and PolarTex-Instant®) and cold-water swelling starches such as (HiForm® and HiForm A™); specialty starches (such as AccuCoat®, AccuFlo™, AraSet™, BatterCrisp®, Clean Set®, DeliTex™, EmCap®, EmTex®, EZ Fill™, and Salioca®); food additives including cellulose; microcristalline cellulose; potato; modified wheat starch; talc; finely ground sugar; icing sugar or powder mix, made of icing sugar, starch, fat and flavor; beet or cane sugar; other sweet sugar solution; fruit juice; honey; caramel; malt; fat; oil; chocolate; cocoa powder; other artificial flavoring; hydrocolloid concentrated solutions (for the purpose of 'sealing' the surface to prevent fat migration, harden the surface, offer a smooth surface to the final glazing application); alcohol-based solutions of resins, essentially shellac resin (for the purpose of 'finishing' the surface to prevent water migration and reducing friction) and others. A particularly useful reference is found on the World Wide Web at http://www.colorcon.com/products-formulation/all-products, the contents of which are incorporated herein by reference. Other ingredients such as vitamins can be incorporated into the coatings of the invention so as to render additional health benefits to the patient during the time period that the patient undergoes treatment with the apparatus and system of the invention.

The coating surrounding the wire increases the diameter of the wire to specific dimensions depending on the size and cross-sectional shape of the wire it coats. In one embodiment of the invention, the coating is a noticeably and distinctively different color than the core wire so that complete dissolution of the coating may be easily confirmed visually.

The coated wire arch form is placed directly on the lingual or facial (labial or buccal) surface of the teeth. Activation of the wire is created via a pulling force with floss, engagement jigs as shown in FIG. 10A, 10B or other means through the contact between the teeth on the contralateral surface, as shown in FIG. 4. The engagement of the jigs to the teeth can be accomplished by any means available and the jigs can be engaged on any side of a tooth that would be necessary for the desired alignment of the teeth. The coated wire is bonded directly to the surface of the teeth (or to the composite bracket-like templates of an alternate embodiment described more fully below) using flowable composite material used in conventional orthodontic techniques.

The dental composites operable within the scope of the invention are any dental composite resins typically used in the dental industry, such as synthetic resins which are used in dentistry as restorative material or adhesives. Examples of composite resins most commonly include bisphenol A glycidyl methacrylate (bis-GMA) and other dimethacrylate monomers, such as triethylene glycol dimethacrylate (TEGMA), urethane dimethacrylate (UDMA), hexanediol dimethacrylate (HDDMA), and a filler material such as silica. Dimethylglyoxime is also commonly added to achieve certain physical properties such as flowability. Further tailoring of physical properties is achieved by formulating unique concentrations and combinations of each constituent.

According to the method of the invention, a "bead" of flowable composite material is applied over the coated wire on each tooth to be aligned. As used herein, the term composite "bead" indicates an application of composite material that is sufficient to attach the wire to the tooth surface. As used herein, the term "bond" or "attach" as referring to the composite material used in the system of the invention means that the composite material is fixedly connected for some period of time by either chemical or physical means to the surface of the tooth.

The composites are bonded herein onto the teeth by either light, chemical activation or heat activation as commonly performed in the dental art. In order to bond the composite to a tooth, the tooth must be kept substantially dry during placement or the resin will likely fail to adhere to the tooth. Composites are placed while still in a soft, dough-like, or flowable state but when exposed to light of a certain blue wavelength (typically 470 nm, with traces of ultra-violet light]), they polymerize and harden onto the tooth. Once properly attached, the composite is comfortable, aesthetically pleasing, strong and durable, and usually lasts throughout the duration of the treatment without the need for reapplication. The composite is typically applied to the tooth by using a syringe. A primer may be used to allow the composite resin to easily infiltrate the surface enamel matrix to bond more strongly to the tooth. A photo-initiator is often added to the composite in order to aid and increase the speed of the curing process of the composite. Prior to applying the composite, the enamel of the teeth may be prepared by etching with 30%-50% phosphoric acid and rinsing thoroughly with water and drying with air only.

Within 1 to 2 hours after being bonded to the patient's teeth (and after the bonding material has cured), the coating surrounding the wire dissolves completely, thus exposing the underlying wire and leaving an aperture or tube within the cured bonding material through which the wire may move freely. By allowing free movement of the now-exposed wire through the aperture(s) in the bonding material, the bonding composite "beads" and apertures operate as a tube similar to a "frictionless bracket system" housing the wire and allowing the now-uncoated wire to express its super-elastic properties and pre-designed arch form, pulling and/or pushing the mal-aligned teeth into conformity with it as it returns to its preformed shape.

Without the apertures or tubes left around the wire by the dissolved coating, the wire would not be free to slide back and forth within the composite beads as it returns to its preformed shape; thus restricted, the force exerted by the wire returning to its preformed shape also would push teeth apart and create space between the teeth or other undesirable tooth movements or not move the teeth at all. Also to be noted is that the composite beads are not limited to any particular shape or geometric configuration, and are limited in size only as to the practical consideration of comfort of the patient within the buccal cavity.

As the teeth align and the wire slides within the tubes formed in the composite beads, the ends of the wire arch form are pushed farther and farther beyond the terminal beads. The ends of the wire arch form may be covered with a bead of composite for comfort or, alternatively, may be pre-formed with smooth ends. Once the wire is activated by being bonded to the teeth or templates, stops of composite, crimpable stops or other stops may be formed or preformed on the arch form ends or between the teeth to prevent the wire arch form from sliding too far and dislodging. As used herein, a "stop" means an element or component positioned on the wire after placement onto the teeth or an element or component that is incorporated into or onto the wire during the fabrication of the wire not encompassed by the flowable composite during wire placement and has a larger dimension than the aperture or tube created by the coating dissolving from the wire. Coated wire arch forms of the system are preferably pre-formed and pre-shaped in various lengths and gauges (sizes), preferably with smooth ends or terminal beads for patient comfort and to act as stops. The stops are created or pre-formed on the ends or midpoint of the wire arch form so as to prevent the wire from slipping out of the composite bonding covering or beads when the teeth align. Though preferably the stops are placed on the ends or midpoint of the wire arch, the stops may be positioned at any location along the wire arch. The coated arch forms can also be custom shaped for any individual and their arch forms.

The wire arch form may be affixed to one or more teeth or templates at the center of the arch or the longitudinal mid-point of the wire, preferably using a tiny bead of composite or incorporated in the arch wire, thus keeping the mid-point of the wire arch form fixed in place (i.e., preventing the wire arch form from sliding out of place) while permitting sliding within the composite beads on either side of the mid-point as the teeth are pushed and pulled into alignment. A tiny bead of composite is one way the midpoint of the wire arch form can be kept in place, but other ways may be devised. The wire is left in place in the mouth until it has returned completely or substantially to its original shape or the teeth are aligned. This typically occurs in 4 to 6 weeks, but may require either less or more time depending on the needs of each patient. The wire arch form is removed by removing the stops or by cutting the wire into segments. If further alignment is desired after the initial placement and activation, the wire can be re-bonded and activated on an individual tooth or be replaced by another coated wire.

In one embodiment, a coated wire arch form comprising a substantially round wire core having a circular cross-section and a dissolvable coating of specific and even thickness is used. In another embodiment, a coated wire arch form comprising a square or rectangular wire core having a coating of specific and even thickness is used. As used herein, the term "rectangular" as referring to the cross section of the wire of the invention shall also encompass embodiments having a square cross section. The preferred diameter of nickel titanium wire core is generally 0.012 inches for round wire core and 0.016×0.022 inches or 0.022×0.016 (at its widest diameter) for rectangular wire core. The coating surrounding the wire core increases the wire's diameter as compared to the uncoated wire. The preferable diameter of the coated wire is enough to create a dimension large enough for the wire to slide in the formed tubes after the coating is dissolved but still staying as thin as possible to allow for the wire to engage the perimeter of the formed tube within the composite bonding surrounding the wire thereby creating the necessary pressure or activation of the wire with a maximum of 0.018 inches for the round wire and 0.018×0.025 inches or 0.025×0.018 for the rectangular wire. In all embodiments, a specific outer dimension of the coated wire may be achieved depending on the choice of wire and the thickness of the coating. It is preferred that the outer dimension of the coated wire be only slightly larger than the diameter of the core wire so that engagement of the core wire in the formed tube be adequate for desired tooth movement yet not interfere with core wire movement. Therefore, it is preferred that the thickness of the coating on the wire is in the range of 0.001 inches to 0.006 inches, such that the total thickness of the wire together with the coating is in the range of 0.013 inches to 0.018 inches.

Where a wire arch of rectangular dimension is used, it is preferred that the rectangular wire has a height that is greater than the depth of the wire as the wire is positioned along the teeth, thus keeping within the objective of the invention in providing an orthodontic appliance with a low in profile within the mouth that is comfortable to the patient, as illustrated in FIGS. 1C and 1D.

In addition the wire, may also incorporate loops 150 or any other shape modification that may assist in tooth movement, as illustrated in FIG. 1E. For example, a loop 150 as part of the wire design, is placed centrally as in FIG. 1F, or on any part of the lateral extensions as in FIG. 1G. These loops 150 may remain exposed or uncovered by bonding adhesive such that each loop can be activated to assist in space closure movements by activation of the terminal ends of the wire. The terminal end of the wire which is beyond or most distal to the loop on either side of the wire is removed from the bonding material which has secured it in position. The wire is then extended thereby opening the loop and generating force with the wire. The extended terminal end of the wire can then be re-bonded to the tooth surface. This causes any space between the teeth to close due to the force generated between the loops of the wire.

According to another embodiment of the invention, composite brackets with a lateral or horizontal groove are provided that are adapted to receive the coated-wire arch form, which are used as an alternative to the composite beads to assist with precise positioning of the wire on the surface of the teeth. The composite brackets preferably are made to fit the contours of the lingual or facial surface of teeth and are placed and bonded to the teeth in the desired positions before application of the coated wire arch form. The bonding or attachment to the teeth is accomplished in the same manner as the composite beads as described hereinabove. Once in place, the coated wire arch form is bonded directly to the bracket. The brackets' grooves may be specifically shaped to effect a pre-programmed torque adjustment (correcting mal-alignment of a tooth's cant or rotation along the labial/lingual or buccal/lingual axis) when used in the system. Preferably, in this torque-adjusting embodiment, bracket grooves have one of a variety of specific rectangular cross-sectional shapes corresponding to the desired torque adjustment, adapted to be used with a pre-shaped arch form of wire with a rectangular cross-section. These brackets may also be used in the continuation of treatment if further activations or increased engagement of the orthodontic wire is necessary to align the teeth. At subsequent visits, any tooth which requires further activation can be reactivated by removing the existing bonded covering of the wire. The direct application of bonding material locks the now non-coated wire and inhibits wire movement due to lack of tube formation. The open end of the bracket can be placed over the wire against the tooth while the wire is reactivated by an external force (floss or other engagement module). The extensions of the brackets may be coated with a thin layer of composite/bonding material or dental adhesive to help secure the bracket in position. Though a composite covering is preferred and is the logical choice based on industry practice, the covering can be made of an alternate functioning material. Flowable bonding material then covers the existing bracket except in the areas of the lateral openings extending over the surface area of the tooth securing the bracket in position. The opening within the bracket acts as an orthodontic tube and allows for the expression of the arch wire to align the teeth. Additionally, an embodiment may contain a groove or slot coated by a metal that is then secured by a composite covering.

In addition to this embodiment, the grooves of the bracket can be prefilled with a dissolvable gel or malleable substance, as illustrated in FIGS. 2B and 2C, into which the non-coated wire is inserted. The gel envelopes the wire within the groove or slot of the bracket, as shown in FIGS. 2D and 2E). While engaging the wire into the slot, the exposed area of the slot is covered with a bead of composite securing the wire in the slot of the bracket (FIG. 2F). The gel-like substance within the groove of the bracket dissolves creating the necessary tube in which the wire can move so as to align the teeth (FIG. 2G). This embodiment can also be used in subsequent appointments for continued tooth movement and alignment of individual teeth after the initial placement of the coated wire.

The gels operable in this embodiment of the invention comprise agar, agar agar, carrageenan iota, carrageenan kappa, gellan gum, lecithin powder or gel, pectin powder or gel, sodium alginate, xanthan gum, as well as other compounds known in the art and interchangeable therewith. As used herein, these and other substances that are operable within the scope of the invention are referred to herein as the "gel".

In addition the dissolvable gel may be applied directly to the tooth surface via syringe or other type of applicator while the now non-coated wire is positioned against the tooth (see FIG. 12.) The gel preferably covers only the area immediately surrounding the wire to minimize the resulting size of tube formation. The wire and gel are covered with composite bonding material and extended over the exposed surface area of the tooth securing the wire into position. As describe above, the gel like substance dissolves and creates a tube within the composite material allowing the nickel titanium wire to express its pre-designed shaped and align the teeth.

In addition to the direct placement of the wire, the system of invention may also be placed into the mouth with a delivery system for ease of engagement and in order to minimize contamination from the oral environment. This system is comprised of a custom tray that is specifically fitted to the teeth and mouth of each patient, in which the coated wire is housed and positioned for proper placement, as illustrated in FIG. 10A. The delivery tray may be composed of plastic or any other materials used in the industry for production of dental trays. The coated wire has the elastic engagement jigs attached and positioned as in FIG. 11. The engagement jigs can be threaded between the teeth activating the wire. The terminal ends of the wire within the plastic tray housing are free to move within the lateral tubes of the housing thus allowing the engagement of the wire to the teeth without resistance. The tubes within the housing should be long enough to prevent the wires from separating and dislodging away from the delivery tray. Once the active part of the wire has been engaged and attach to the lingual surface of the teeth, the delivery system is removed by cutting the arch wire at the terminal beads of composite and cutting each individual engagement jig at the surface of the coated wire.

In this respect, before explaining at least one embodiment of the invention in detail, it is to be understood that the invention is not limited in its application to the details of processes, steps, or construction, or to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

DESCRIPTION OF THE DRAWINGS

FIG. 1A—Perspective view of two different embodiments of the coated wire arch form of the invention, one with a round cross-section and one with a rectangular cross section.

FIG. 1B—Cross-sectional view of the two embodiments of the coated wire arch form depicted in FIG. 1A.

FIG. 1C—Longitudinal view of the coated rectangular wire showing the dimension of the wire being greater in height than width.

FIG. 1F—A view of one embodiment of the wire according to the invention showing an individual arch form with a centrally located loop.

FIG. 1G—A view of an alternate embodiment of the wire according to the invention showing an individual arch form with loops as part of its design located on its lateral extensions as illustrated in FIG. 1E.

FIG. 2—Front elevational view of a composite bracket of one embodiment of the invention, said bracket having a lateral groove to hold the coated orthodontic wire in the desired position before bonding.

FIG. 2A—Side view of the composite bracket of FIG. 2.

FIG. 2B—Frontal view of the embodiment showing the gel positioned in the groove of the bracket.

FIG. 2C—Cross-sectional view of the embodiment showing the gel within the groove of the bracket.

FIG. 9—Occlusal view of the maxillary arch showing placement of a delivery tray to assist in the placement of the invention. The tray covers the posterior portion of the arch and is open in the anterior segment in the area of wire delivery. The wire arch form is held in place by "micro tube housing" which allows the wire to slide into position.

FIG. 10A—Occlusal view of the maxillary arch showing arch wire positioned within a delivery tray with engagement jigs attached to the surface of the coated portion of the arch wire.

FIG. 10B—Top and side close-up view of engagement jigs showing details of its structure and components.

FIG. 11—Occlusal view of the maxillary arch showing wire engagement against the teeth utilizing the delivery tray and engagement jigs.

Figure 1D:
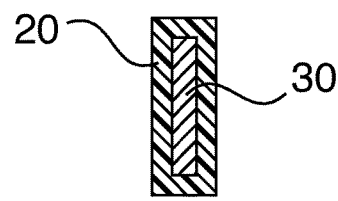
FIG. 1D—Cross sectional view of the embodiment of FIG. 1C with rectangular measurements greater in height than width.
Figure 1E:
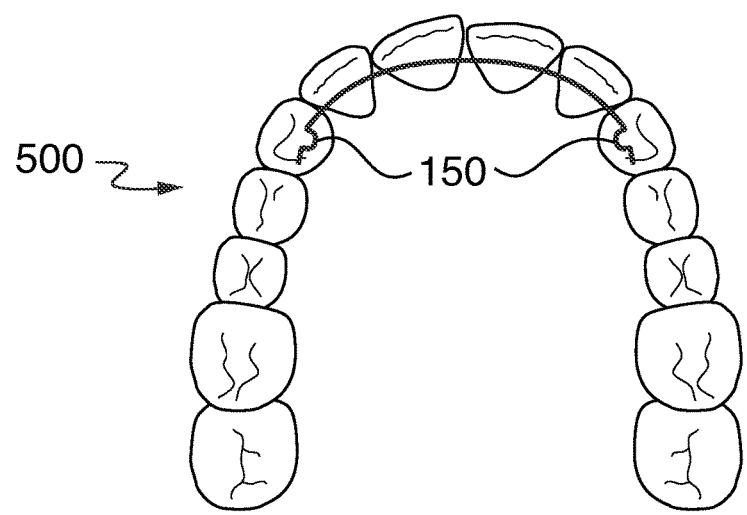
FIG. 1E—Occlusal view of the maxillary arch of the mouth of a patient showing an embodiment of the wire according to the invention with bilateral loop formations in it design.
Figure 1F:
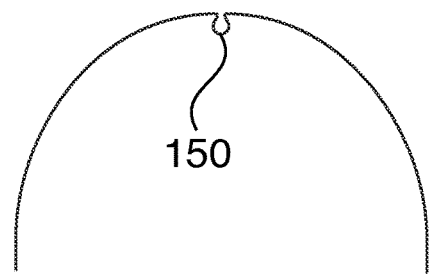
Figure 1G:
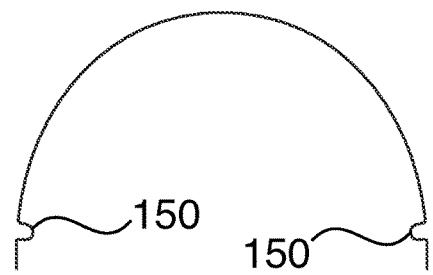

It should be understood that the above described figures are not intended to limit the scope of the present invention in any way and are intended to illustrate the embodiments of the invention.

DETAILED DESCRIPTION OF THE PREFERRED EMBODIMENT

Referring now to FIG. 1A, two embodiments of the wire arch form of the invention are shown. The coated round orthodontic arch form 100 comprises a round wire core 30, preferably of nickel titanium, substantially coated at a substantially even thickness with a non-toxic coating adapted to dissolve upon prolonged (preferably no less than 1 hour) exposure to moisture, heat, oral fluids or any combination thereof. An alternate embodiment uses an arch form with a rectangular cross-section 100. The coated rectangular orthodontic arch form comprises a rectangular wire core 30, preferably of nickel titanium, substantially coated at a substantially even thickness with a non-toxic coating adapted to dissolve upon prolonged (preferably no less than 1 hour) exposure to moisture, heat, oral fluids or any combination thereof. Alternatively, the coating is a substance that withstands prolonged exposure to moisture, heat and oral fluids but readily dissolves upon contact with a non-toxic triggering solution. In all cases, the coating should not interfere with the super-elastic properties of the pre-formed arch wire and should be non-toxic and substantially non-irritating.

The wire core 30, is preferably nickel titanium, but wire made of any metal or other material with similar super-elastic properties, including copper NiTi (copper-zinc-aluminum-nickel, copper-aluminum-nickel), Sentalloy®, Neo Sentalloy® and Bioforce® wires or any other super-elastic wires or wires with ion-implantation process, may be used. The round wire core 30 has a preferred diameter of 0.012 inches, but a round core having a diameter from 0.010 inches to 0.017 inches is operable. The cross-section of the rectangular wire core 30 of the invention can be in the range of 0.012 inches to 0.022 inches. The rectangular core 30 has a preferred diameter of 0.012×0.018 inches, but a rectangular core having a diameter from 0.012×0.018 inches to 0.016× 0.022 inches is also operable within the scope of the invention.

FIG. 1B shows the dissolvable non-toxic coating 20, which is preferably composed substantially of gelatin or any non-toxic dissolvable coating with lubricating properties like titanium dioxide (TiO2), similar to that used to coat tablets and form capsules for oral medicinal use, such as Kollicoat® (available from BASF), but any non-toxic dissolvable coating which does not interfere with the super-elastic properties of the wire core 30, may be used. Because the dissolvable coating substantially coats the wire core at a substantially even thickness around and along the wire core 30, the dissolvable coating conforms to the shape of the wire core, increasing its diameter without altering its cross-sectional or longitudinal shape. The preferable diameter of the coated wire arch form is 0.018 inches, but a diameter as low as 0.012 and preferably in the range of 0.013 inches to 0.018 inches is operable, it being understood that the diameter of the coated wire depends on the diameter of the wire core.

Referring now to FIG. 1B, cross sections of the round coated wire arch form 100 and rectangular coated wire arch form 100 are shown. Referring to the depiction of arch form 100, the rectangular wire core 30 and dissolvable coating 20 of substantially even thickness is shown in cross-section. Referring to the depiction of arch form 100, the round wire core 30 and dissolvable coating 10 of substantially even thickness is shown in cross-section. Referring to FIG. 1C, the longitudinal view of the rectangular core wire 30 wherein the height of wire is greater than its depth. FIG. 1D is a cross-sectional view of the core wire 30 with coating 20.

Referring now to FIG. 2, a front elevational view of the composite bracket embodiment of the invention is shown. The composite bracket 300 assists with the precise positioning of the orthodontic wire 100 on the surface of teeth before the wire arch form is bonded to the teeth. Preferably, composite bracket 300 conforms to the contours of the tooth to which it will be applied, and generally has a top edge 50 and a bottom edge 60. In one embodiment, the top edge 60 and bottom edge 50 are substantially parallel, but the exact shape of each composite bracket will vary as each is designed to fit the specific contours of individual teeth. Each composite bracket 300 has a lateral groove 55 in its surface 70 extending substantially across its entire width adapted to hold the coated orthodontic wire arch form in place for bonding. Preferably, the groove 55 bisects the bracket widthwise at substantially its midpoint.

Each composite bracket 300 is placed where desired and bonded to the teeth, before application of the wire arch form, using known orthodontic bonding techniques, such that the grooves in each bracket align to form a guide for proper placement of the arch form. The grooves 55 are adapted to hold a coated orthodontic wire arch form 100 in place by being of sufficient depth and diameter and sufficiently conforming shape that the arch form 100 is movably captured with enough friction fit to resist slipping or falling but not so tightly that the arch form cannot be easily adjusted during placement. The optimal dimensions of the grooves 55 are 0.018 inches deep and 0.018 inches in diameter measured at the surface of the bracket as shown in FIG. 2A. As illustrated on the FIG. 2A, the diameter of the groove is the distance measured from point a to point b along the plane of the bracket's surface. Once in place, the orthodontic wire arch form is bonded to each composite bracket 300 using flowable composite beads as described herein.

Figure 2D:
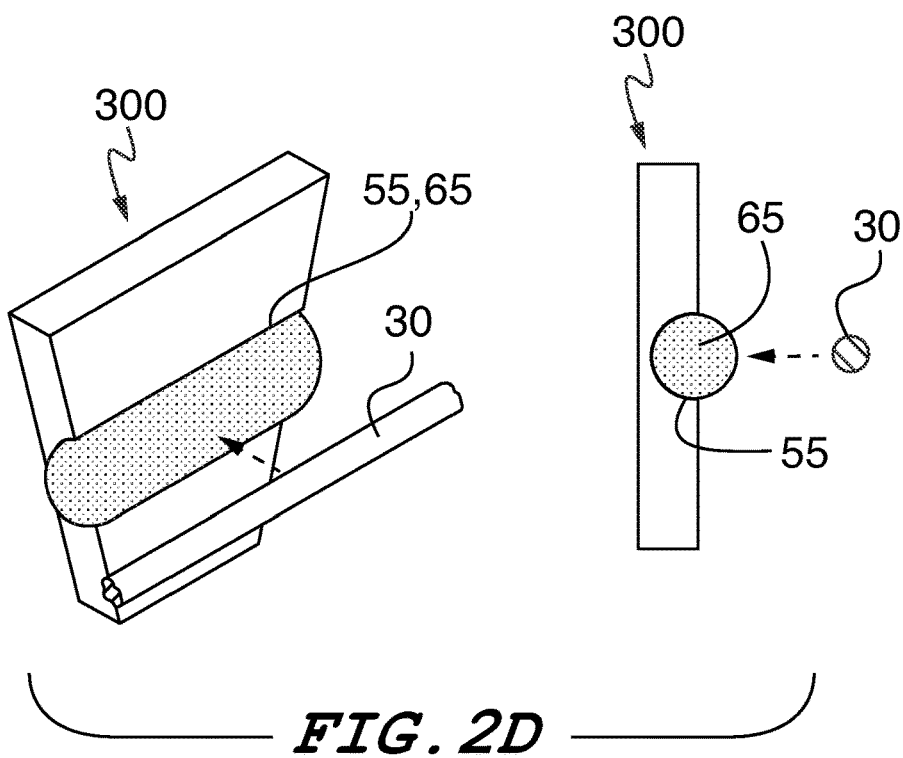
FIG. 2D—Frontal and cross-sectional view of the bracket with the gel within the groove and non-coated core wire outside of the bracket groove.
Figure 2E:
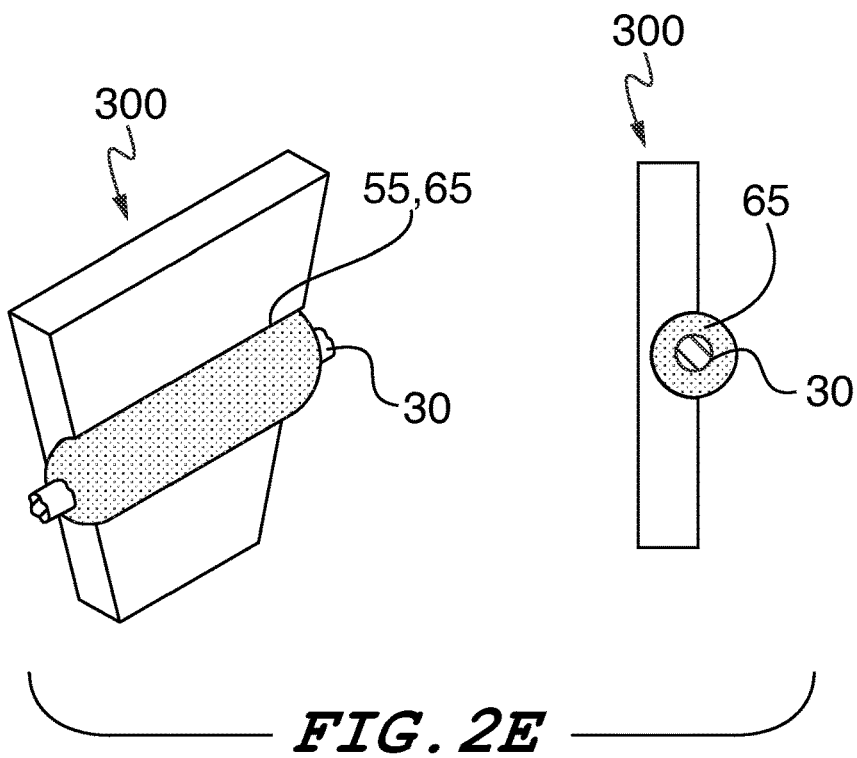
FIG. 2E—Frontal and cross-sectional view of the bracket with non-coated core wire inserted into the gel.
Figure 2F:
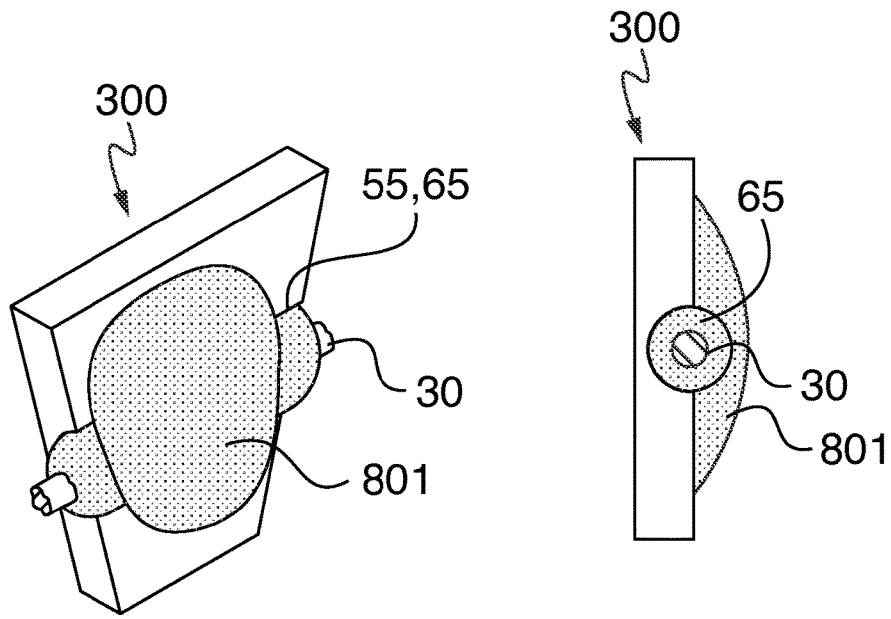
FIG. 2F—Frontal and cross-sectional view of the bracket and wire with the composite bead covering the open area of the groove locking the wire in place within the gel.
Figure 2G:
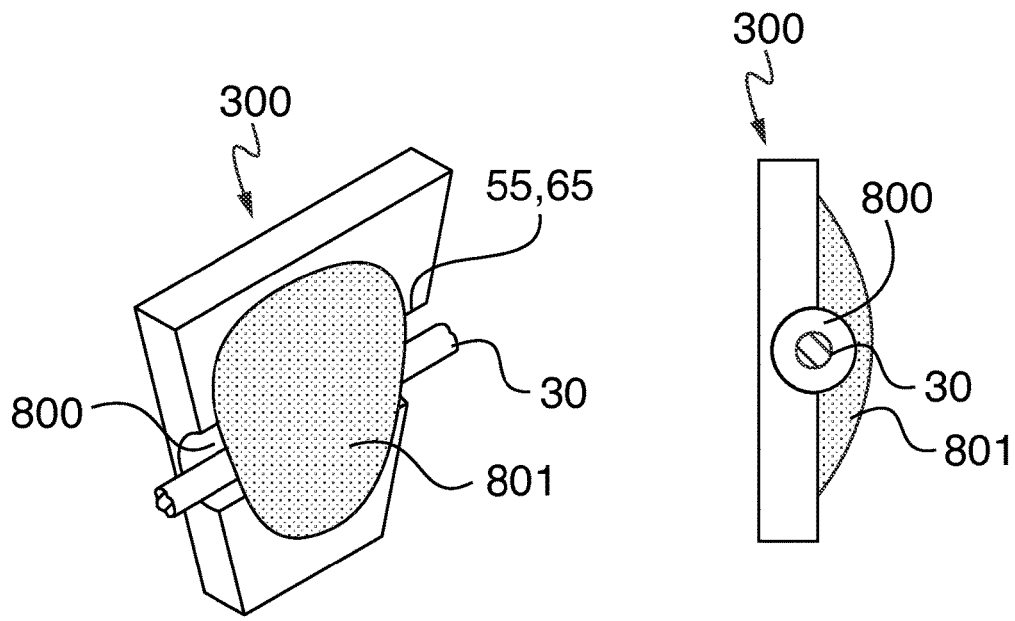
FIG. 2G—Frontal and cross-sectional view of the bracket with non-coated core wire and composite bead. The gel has dissolved and created an aperture or tube around the wire.

FIGS. 2B (frontal view) and 2C (cross-sectional view) show the dissolvable gel 65 held within the lateral groove 55 of bracket 300. Lateral groove 55 has a preferred width of 0.013-0.018 inches. FIG. 2D shows a non-coated wire 30 prior to placement into lateral groove 55. FIG. 2E shows the non-coated wire inserted into the gel 65 and the lateral groove 55. FIG. 2F shows placement of the composite covering 801 over the exposed groove area of the bracket holding the wire in place within the gel 65 and lateral groove 55, which is held in place by covering 801. FIG. 2G shows the formation of the aperture or tube 800 within the bracket by the dissolved gel 65. The core wire 30 is now capable of movement within the bracket 300. This feature of the embodiment allows for the non-coated core wires 30 to be placed in the bracket and the tube formation to be within the bracket when the gel within the lateral groove 55 has dissolved. These gel filled brackets can be used at the initiation of treatment using multiple brackets or singularly at subsequent appointments to reactivate individual teeth after the core wire has been exposed.

Figure 3:
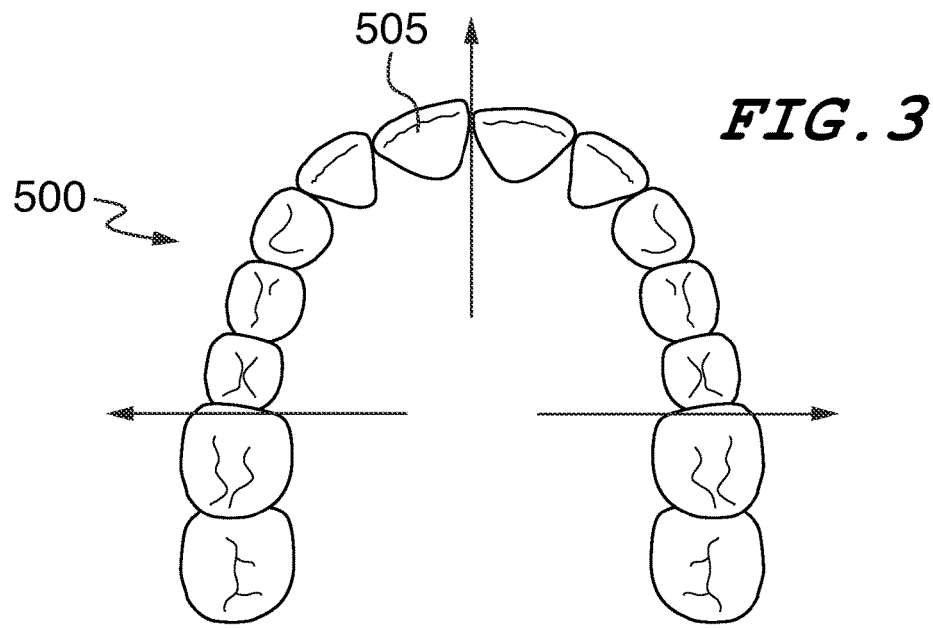
FIG. 3—Occlusal view of a maxillary arch showing mal-alignment of the anterior teeth.
Figure 4:
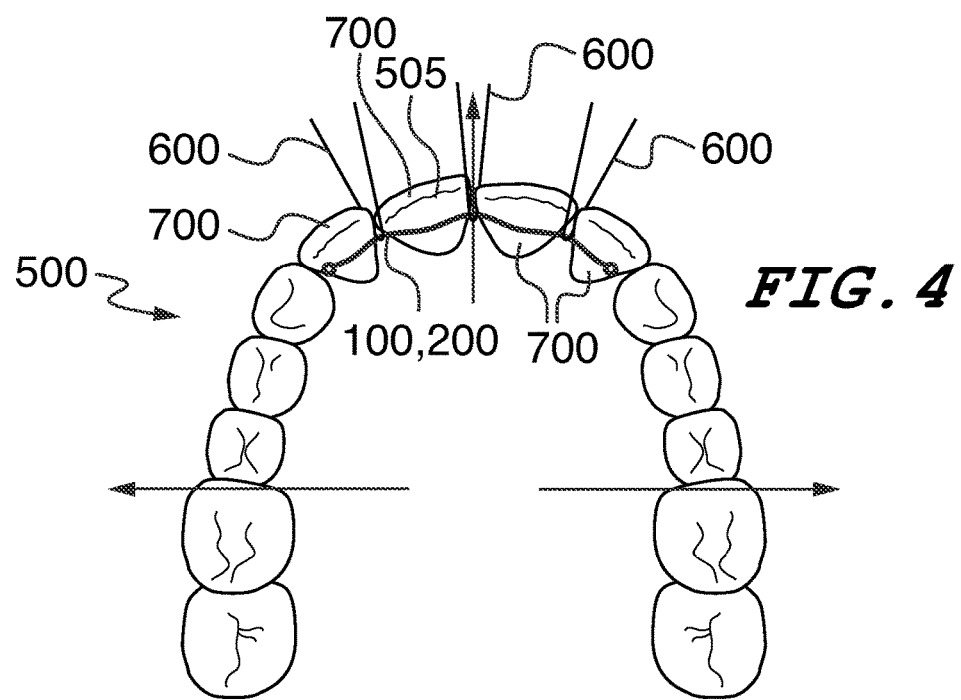
FIG. 4—Occlusal view of the maxillary arch of FIG. 3 with the coated orthodontic wire pulled into position via floss in contact with the lingual surface of the maxillary anterior teeth to be aligned.
Figure 5:
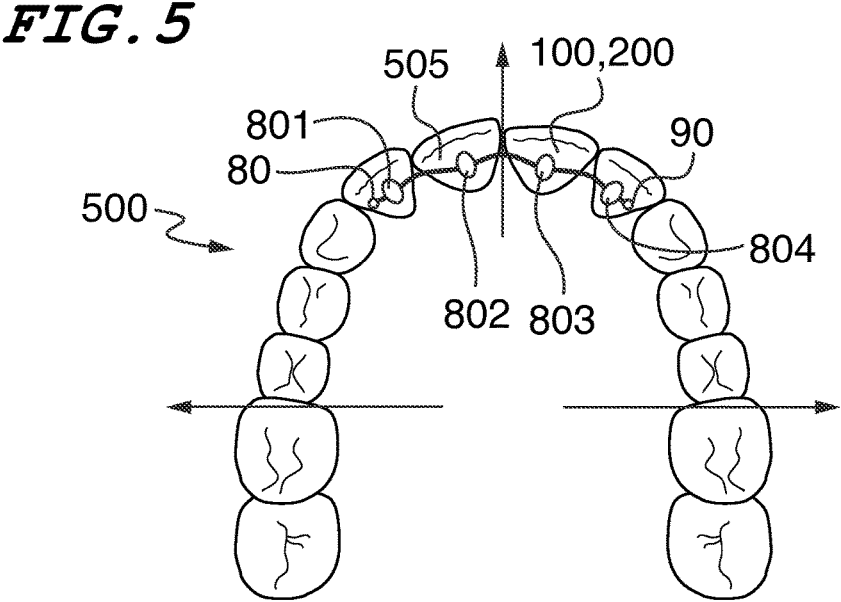
FIG. 5—Occlusal view of the maxillary arch and orthodontic wire of FIG. 4 with composite beads placed on the individual teeth covering the wire.

FIGS. 3-5 depict the occlusal view of a maxillary arch 500 showing mal-alignment of the anterior teeth, specifically the front-right incisor 505. FIG. 4 shows the application of the coated wire arch form according to the invention to the lingual surface of the teeth of FIG. 3. The system and method may alternatively be used to apply the arch form to the facial surface of teeth. Likewise, use of the system and method to correct mal-aligned of maxillary teeth is shown, but the system and method may alternatively be used to correct misaligned mandibular teeth as well. Referring now to FIG. 4, floss 600 is wrapped around the coated orthodontic wire arch form 100 between the teeth to place the coated wire arch form into the desired position on the lingual surface of the anterior teeth 700 and to pull the arch form tightly between each piece of floss to increase contact of the coated wire to the surface of the teeth.

Demonstrated in FIG. 5, the coated wire arch form 100 is secured to the lingual surface of the anterior teeth via composite beads 801, 802, 803, 804 of flowable composite material using known orthodontic techniques. Preferably, left end 80 and right end 90 of the coated wire arch form 100 extend past the terminal composite beads 801 and 804, respectively. The optimal distance of extension beyond each terminal composite bead when applied is preferably in the range from 1 mm to 2 mm.

Figure 6A:
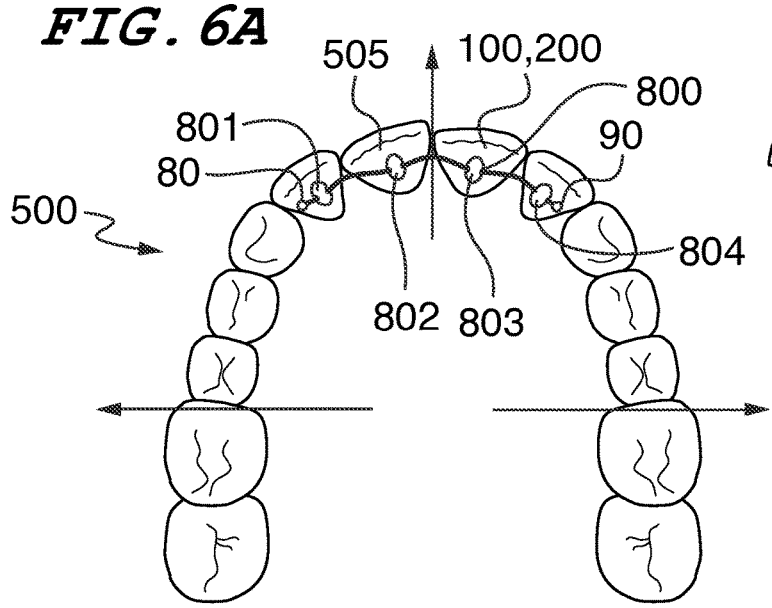
FIG. 6A—Occlusal view of the maxillary arch, orthodontic wire and composite beads of FIG. 5 showing the orthodontic wire after the coating has dissolved.
Figure 6B:
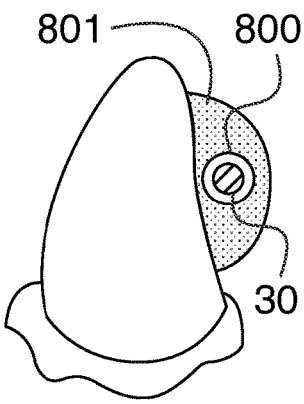
FIG. 6B—Cross-sectional view of a composite bead showing the aperture left after dissolution of the wire's coating.

FIGS. 6A and 6B depict the wire arch form after the coating has dissolved. Only the wire core 30, will remain, leaving an aperture or tube 800 (shown in FIG. 6A) in the composite bead 801, 802, 803, 804. The exposed ends of the wire arch form may be covered by beads of composite for comfort, (bead 80 shown on left end of wire and right end bead 90 is shown on the right end of the wire). Alternatively, the wire arch form may have prefabricated smooth ends.

Figure 7:
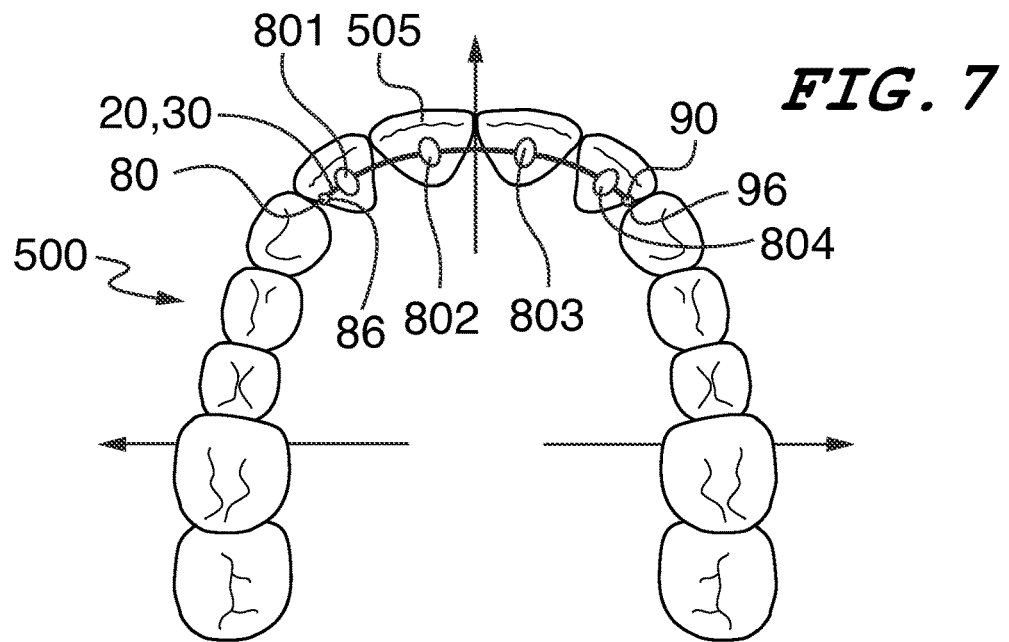
FIG. 7—Occlusal view of the maxillary arch, orthodontic wire and composite bead of FIG. 6A showing the wire after its return to its preformed shape and showing the anterior teeth in proper alignment.

Over the course of a period of time (in the range of 4 weeks to 8 weeks, depending on the patient), the now-uncoated wire arch form 30 returns to its preformed shape, pulling teeth into alignment with it. Referring now to FIG. 7, the maxillary arch of FIG. 6B is shown after the uncoated wire arch form 30 has returned to its preformed shape and the mal-alignment in the right incisor 505 has been corrected. The ends of the arch form, with terminal beads 80, 90 for comfort, are shown extended a greater distance beyond their position of FIG. 6B, as the force exerted by the wire arch returning to its preformed shape has pushed the ends of the wire further beyond the terminal composite beads, due to free movement of the wire within the apertures of the composite beads, instead of pushing the teeth apart. Wire stops or composite beads may be applied to the terminal ends of the wire arch form or between the teeth to prevent the wire arch form from dislodging.

Figure 8:
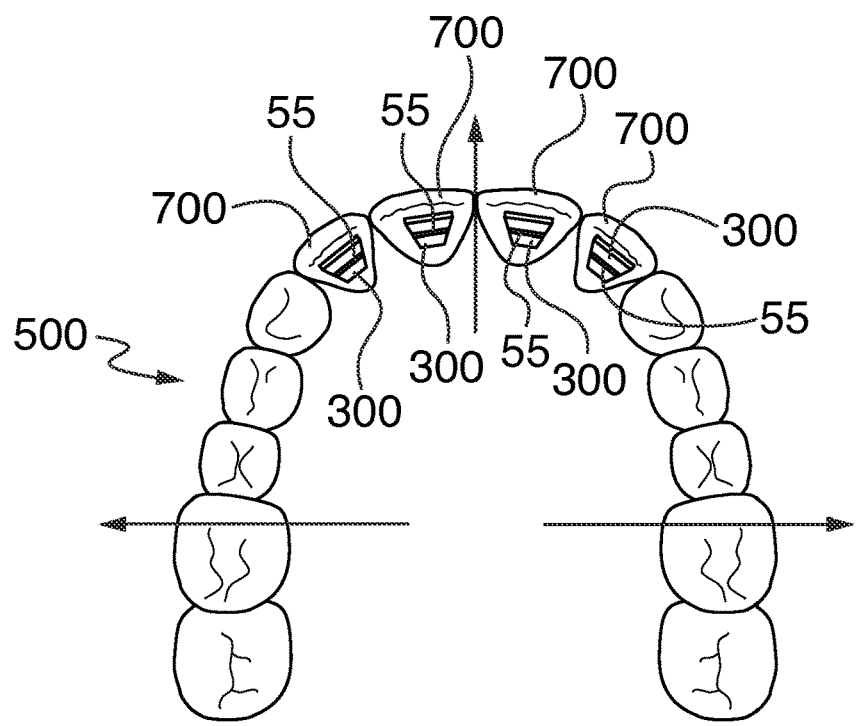
FIG. 8—Occlusal view of a maxillary arch showing placement of composite brackets on the lingual surface of anterior teeth to aid in precise placement of the coated orthodontic wire arch form before bonding.
Figures 15, 16:
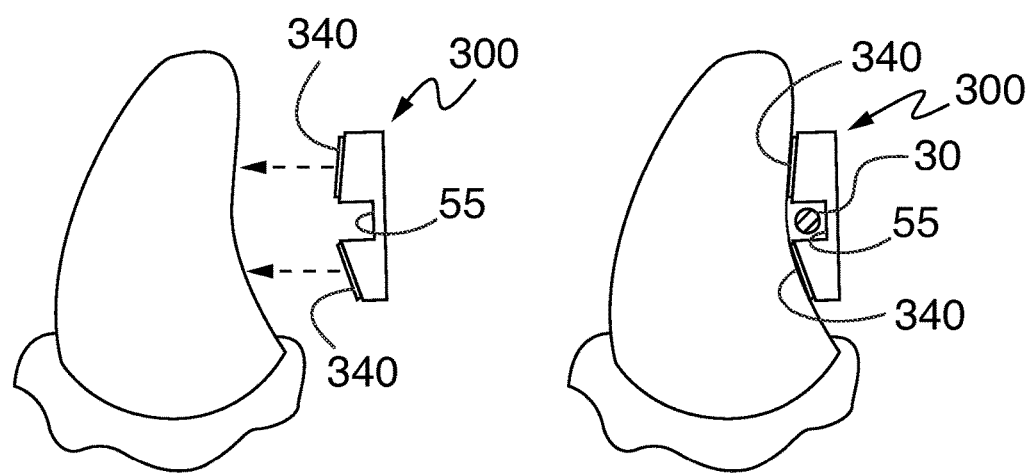
FIG. 15—A perspective view of a tooth together with a composite bracket having a groove facing the surface of the tooth and the composite bracket having a thin layer of composite material or dental adhesive for attaching to the tooth.
FIG. 16—A perspective view of the tooth and composite bracket of FIG. 15 wherein the bracket is bonded to the tooth and showing a round cross-section of the arch wire of the invention within the groove of the bracket.

Referring now to FIG. 8, an alternate embodiment of the system and method is partially shown. Brackets 300 preferably made of orthodontic composite material are shaped to conform to the contours of specific teeth and have a lateral groove 55 extending across their widths preferably bisecting them at substantially their midpoints. The brackets enable precise positioning of the coated wire arch form before it is bonded. Brackets may be made with grooves 55 or notches of one of a variety of particular, pre-programmed shapes, preferably rectangular shapes, adapted to cause a desired torque adjustment on a particular tooth or teeth when used with the system and in particular with the pre-shaped arch forms of the invention, preferably those having a rectangular cross-section. Brackets are first placed and bonded to the lingual or facial surface of the teeth using known orthodontic techniques such that their grooves align to form the desired placement of the coated wire arch form. The grooves of the brackets may be protected with a removable covering to prevent excess bonding material from blocking or filling the grooves, which covering is then removed once the brackets are in place and bonded to the surface of the teeth. The grooves may also be filled with a dissolvable and malleable gel 65 (FIG. 2E) in which a non-coated wire is inserted into the gel which coalesces around the wire (FIG. 2F). FIG. 15 illustrates a close up perspective view of one tooth together with a composite bracket of FIG. 8, showing lateral groove 55 facing the surface of the tooth and the composite bracket 300 having a thin layer of composite material or dental adhesive 340 for attaching to the tooth. FIG. 16 further illustrates a perspective view of the tooth and composite bracket of FIG. 15 wherein bracket 300 is bonded to the tooth and shows a round cross-sectional arch wire 30 within the groove 55 of the bracket.

The coated wire arch form is placed in position and movably held there by friction fit with the brackets' grooves or by force generated against the wire via floss or other form of engagement jig (FIG. 10A) as described above, or by alternative means of force to position the wire in the bracket groove and hold it there while it is being bonded in place. The dimensions of the brackets' grooves correspond to the dimensions of the coated wire arch form, preferably sufficiently to hold the coated wire arch form in place but not hold it so tightly that the arch form may not be easily adjusted before bonding. Once the coated wire arch form is in position and held there by friction fit, pulling force via floss or other external force, the coated wire arch form is bonded in place using beads of flowable composite as in FIG. 5, except that instead of being bonded to the surface of the teeth as in FIGS. 5 and 6, the coated wire arch form is bonded to the brackets (which have already been bonded to the surface of the teeth as previously described). Thus, in the embodiment making use of brackets as partially illustrated in FIG. 8, each aperture left after dissolution of the coating, if not entirely within a composite bead, is between the composite bead and the bracket (particularly the groove of the bracket), rather than between the composite bead and the surface of the tooth, as in the embodiment without brackets partially illustrated in FIGS. 5 and 6.

Figure 12:
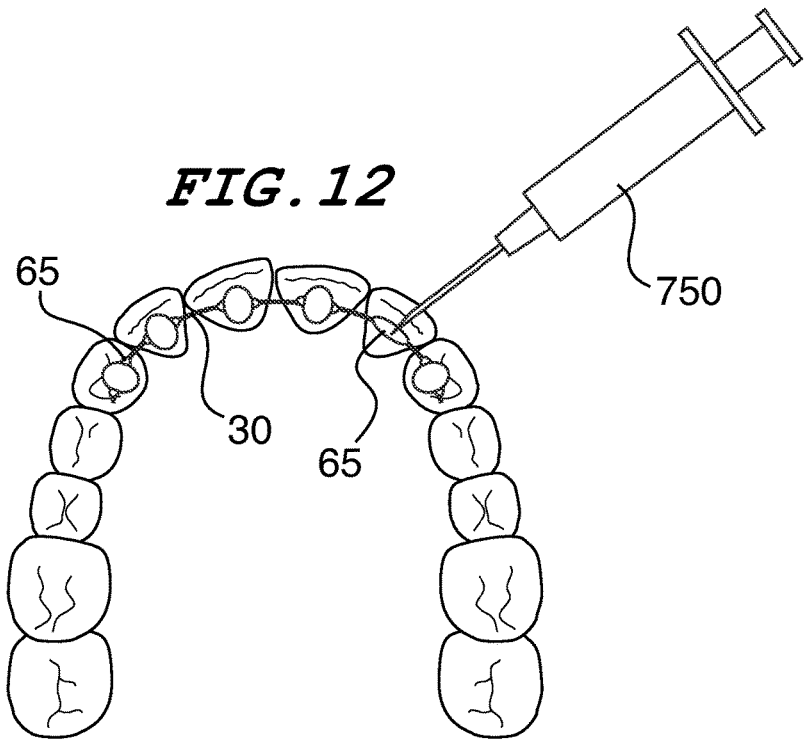
FIG. 12—Occlusal view of the maxillary arch with the orthodontic wire of the invention showing application with a syringe of the gel onto a tooth.
Figure 13:
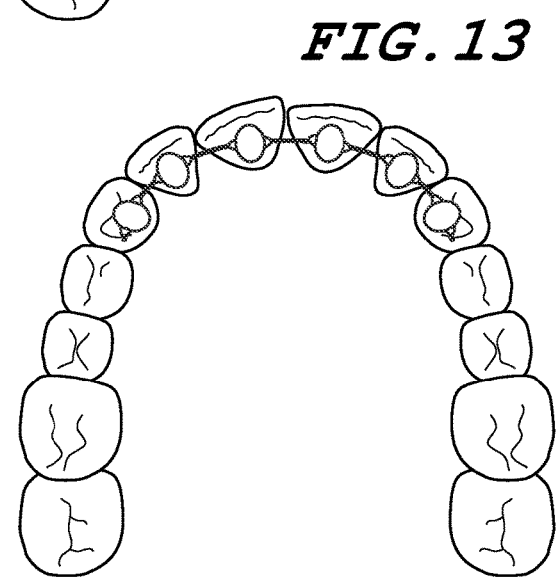
FIG. 13—Occlusal view of the maxillary arch showing the composite bonding over dissolvable gel coating.
Figure 14:
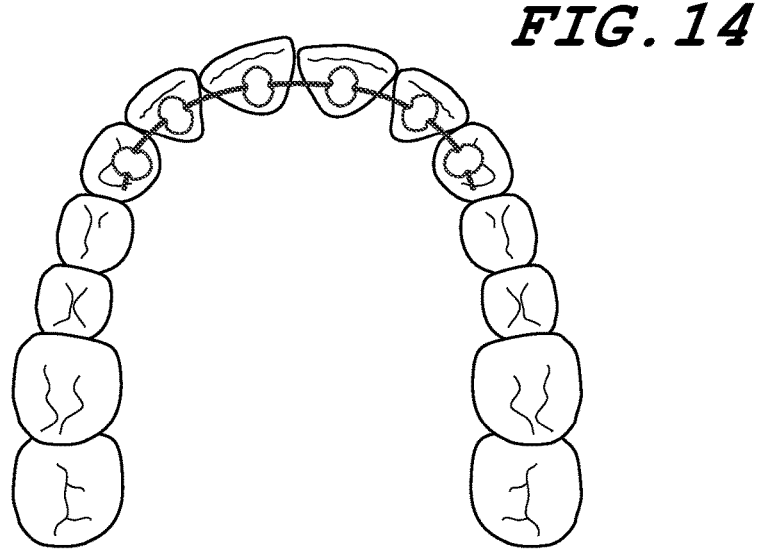
FIG. 14—Occlusal view of the maxillary arch showing an aperture or tube formation under a composite bead.

FIG. 12 illustrates the occlusal view of the maxillary arch with the orthodontic wire of the invention 30 showing application with a syringe 750 of the gel 65 onto a tooth. FIG. 13 illustrates the occlusal view of the maxillary arch with an embodiment showing the orthodontic wire of the invention showing a bead of composite covering the wire and gel and attached to the tooth. The application of the gel with the syringe is particularly useful as part of the process of the invention for follow up appointments after initial placement of the wire in order to re-activate individual teeth. FIG. 14 illustrates the occlusal view of the maxillary arch with the orthodontic wire of the invention showing a bead of composite covering the wire wherein the gel has dissolved and created a tube or aperture under the composite bead surrounding the orthodontic wire.

Referring now to FIG. 9, illustrated is a method delivering the system of the invention to the teeth and mouth in order to help position and deliver the wire to an individual patient with ease and control. The method provides a delivery tray 900 which is custom made to a three-dimensional model representation of the patient's arch 500. Tray 900 has specifically positioned "micro tube housing" 950 on both sides of the tray holding and securing the arch wire to the teeth. The coated portion of the wire 100 is positioned in the open portion of the tray 900 in the area for which it is adhered to the teeth. The non-coated core wire extensions 30 are engaged in the "micro tube housing" 950 holding the wire in its position. The "micro tube housing" 950 is preferably long enough to hold an extension of the core wire 30 in which the wire can slide through the micro tube housing 950 without dislodging.

FIG. 10B illustrates another component of the delivery system which incorporate engagement jigs (shown in FIG. 10A) which are attached to the main wire and positioned between each contact 901-907. These engagement jigs are made of an elastic material preferably, such as, silicone or rubber like materials in which the jig can be stretched and threaded between the contacts of the teeth pulling the wire into position and securing the wire while being bonded to the tooth surface as illustrated in FIG. 11. Once the wire is bonded in place, the individual jigs may be removed by pulling on the smaller extension away from the wire and trimming with a cutting instrument. The remainder of the delivery tray can be removed after trimming the wire at the terminal composite beads.

It is to be understood that the present invention is not limited to the embodiments described above or as shown in the attached figures, but encompasses any and all embodiments within the spirit of the invention.

What is claimed is:

1. An orthodontic apparatus for repositioning one or more of a plurality of teeth, the apparatus comprising:
   an arch-shaped arch wire for attachment to the one or more teeth, and following contour of dental morphology of the plurality of teeth; and
   a bead-shaped rigid monolithically formed composite material for causing the arch wire to apply force to the one or more of the plurality of teeth;
   the monolithically formed composite material forms an aperture or tube that completely encircles the arch wire with space between the arch wire and the monolithically formed composite material so that the arch wire is capable of touching the entirety of the monolithically formed composite material that forms the aperture or tube;
   wherein the arch wire under tension is slidable within the aperture or tube.

2. The orthodontic apparatus of claim 1, wherein the arch wire includes a metal selected from a group consisting of: nickel titanium, copper nickel titanium, beta titanium, copper-zinc-aluminum-nickel, copper-aluminum-nickel, and stainless steel.

3. The orthodontic apparatus of claim 1, wherein the arch wire includes a metal selected from a group consisting of: super-elastic nickel titanium and heat activated nickel titanium.

4. The orthodontic apparatus of claim 1, wherein the composite material includes a composite resin.

5. The orthodontic apparatus of claim 4, wherein the composite material comprises bisphenol A glycidyl methacrylate (bis-GMA) and other dimethacrylate monomers selected from a group consisting of: triethylene glycol dimethacrylate (TEGMA), urethane dimethacrylate (UDMA), and hexanediol dimethacrylate (HDDMA), silica and dimethylglyoxime.

6. The orthodontic apparatus of claim 1, wherein the system imparts force in one or more directions on the one or more teeth when the system is placed onto the one or more teeth and repositions the one or more teeth from a first arrangement to a successive arrangement.

7. The orthodontic apparatus of claim 1, wherein the arch wire is prefabricated before being placed onto the one or more teeth of the patient.

8. The orthodontic apparatus of claim 1, further comprising at least one stop on the arch wire to prevent the arch wire from slipping out of the composite material.

9. The orthodontic apparatus of claim 8, wherein the at least one stop is located on separate end points of the arch wire.

10. The orthodontic apparatus of claim 1, wherein the arch wire has a substantially round cross-section and a diameter of the substantially round cross-section is in a range of 0.012-0.018 inches.

11. The orthodontic apparatus of claim 1, wherein the arch wire has a rectangular cross-section with a widest dimension, and the widest dimension of the rectangular cross-section is in a range of 0.016 to 0.025 inches.

12. The orthodontic apparatus of claim 1, wherein the arch wire further incorporates at least one loop.

* * * * *